(12) United States Patent
Caporal Piotrovski

(10) Patent No.: US 8,882,086 B2
(45) Date of Patent: Nov. 11, 2014

(54) RECHARGEABLE AND RESTERILIZABLE MIXING DEVICE WITH PHYSIOLOGICAL GAS AND SOLUTION TO CREATE FOAM WITH MICROBUBBLES, USED IN ENDOVASCULAR TREATMENTS

(76) Inventor: Murillo Caporal Piotrovski, Florianópolis (BR)

( * ) Notice: Subject to any disclaimer, the term of this patent is extended or adjusted under 35 U.S.C. 154(b) by 67 days.

(21) Appl. No.: 13/580,202

(22) PCT Filed: Sep. 13, 2011

(86) PCT No.: PCT/IB2011/054005
§ 371 (c)(1),
(2), (4) Date: Aug. 21, 2012

(87) PCT Pub. No.: WO2013/038231
PCT Pub. Date: Mar. 21, 2013

(65) Prior Publication Data
US 2013/0190802 A1    Jul. 25, 2013

(51) Int. Cl.
| | | |
|---|---|---|
| *B01F 3/04* | (2006.01) | |
| *B05B 7/26* | (2006.01) | |
| *A61B 17/12* | (2006.01) | |
| *B05B 7/00* | (2006.01) | |
| *B05B 7/24* | (2006.01) | |

(52) U.S. Cl.
CPC ......... *A61B 17/12186* (2013.01); *B05B 7/2472* (2013.01); *B05B 7/267* (2013.01); *B05B 7/0037* (2013.01)
USPC .......................................... 261/115; 261/116

(58) Field of Classification Search
USPC ................................. 261/115, 116
See application file for complete search history.

(56) References Cited

U.S. PATENT DOCUMENTS

2006/0049269 A1    3/2006    Osman et al.

FOREIGN PATENT DOCUMENTS

| | | |
|---|---|---|
| BR | PI 0407003-8 | 1/2006 |
| BR | PI 0414281-0 | 11/2006 |
| DE | 35 20 044 A1 | 12/1986 |
| EP | 1 647 255 A2 | 4/2006 |
| EP | 1 935 605 A1 | 6/2008 |
| GB | 2 369 996 A | 6/2002 |
| JP | 2000000447 A * | 1/2000 |

OTHER PUBLICATIONS

International Search Report of PCT/IB2011/054005, May 7, 2012.

\* cited by examiner

*Primary Examiner* — Robert A Hopkins
(74) *Attorney, Agent, or Firm* — Marshall, Gerstein & Borun LLP

(57) ABSTRACT

A mixer to create foam with microbubbles using physiological gases currently used in sclerotherapeutic treatments of varicose veins has anatomical and compact dimensions and is built with material resistant to sterilization and pressure. The device is mounted on the body around an essentially cylindrical axle comprised of a central valve support, while the top conical body portion is crossed in its center by a flow orienting duct. This axle is coupled at the center of a spinning circular reservoir constituted by the body, containing several housings for the application of solutions with different concentration levels. These parts are locked by a connector at the bottom to the gas duct with a spray nozzle. Each housing has a channel that can be aligned to communicate with the inside of the flow orienting duct of the central axle, responsible for orienting the produced mixture to a top reservoir with a foam-making nozzle.

2 Claims, 7 Drawing Sheets

RECHARGEABLE AND RESTERILIZABLE MIXING DEVICE WITH PHYSIOLOGICAL GAS AND SOLUTION TO CREATE FOAM WITH MICROBUBBLES, USED IN ENDOVASCULAR TREATMENTS

CROSS REFERENCE TO RELATED APPLICATIONS

This application is the National Stage of PCT/IB2011/0584005 filed on Sep. 13, 2011, the disclosure of which is incorporated by reference. The international application under PCT artical 21(2) has not yet been published This patent application refers to a rechargeable, resterilizable, portable, and easy-handling reservoir to create foam with microbubbles using physiological gases; foam currently used in sclerotherapeutic treatments of varicose veins. It may be used also to create foam for other therapeutic purposes by endovascular means.

This reservoir has anatomical and compact dimensions and is elaborated with material resistant to sterilization and pressure, designed to be used in treatments at doctor's offices, clinics or hospital centers.

BACKGROUND OF THE INVENTION

As widely known, the endovascular treatment is carried out inside vessels in order to treat circulatory diseases in blood vessels, arteries, or veins.

Sclerotherapy is the name given to the method that consists of the injection of some product into varicose veins in order to sclerose them.

Today, a liquid widely used in this method is the hypertonic glucose. It is often used separately in a concentration of 75% or lower (50%), with the addition of another substance to increase its sclerosing capacity.

The foam is applied in this context, that is, in order to increase the sclerosis capacity. It consists of the mixing of a medication, currently Polydocanol or tetradecil-sulphate, mixed with regular air and then vigorously agitated to form a dense foam that, when injected in the varicose vein, remains in contact with it for a longer period for being denser than the liquid, thereby increasing its sclerosing capacity and enabling the treatment of varicose veins larger than 0.4 cm in diameter.

In current treatments, a liquid or foam is used and referred to as sclerosants, which are injected through needles of several sizes, depending on the size of the vein to be treated. This liquid or foam causes an alteration in the blood vessel wall cells that later causes its occlusion. When the liquid or foam remains in the circulation, it is diluted by the blood and loses its concentration and effect.

The foam used today is produced in a homemade way, using syringes, a three-way key, regular air, and a liquid, This foam contains irregular, large bubbles, which dilute its density and cohesion. Consequently, this homemade foam dilutes more easily inside the blood stream and loses its function, which is to lesion the internal wall of the varicose vessel. That is, it is less effective when compared with foam with microbubbles.

In order to obtain the microbubbles, a chemical sclerosing foam of good quality has to be prepared with a detergent solution and physiological gases under properly calibrated pressure that, when injected in the vessel, provides better density and higher efficacy in the treatment of larger varices. The use of physiological gases allows physicians to use a higher quantity of foam in each treatment session with higher safety, providing better and quicker results in the proposed treatment. This new technique using foam with microbubbles is less invasive, does not require resting periods, and the patient does not have to interrupt its daily activities as the procedure is not surgical.

PRIOR ART

Reservoirs or equipments intended to create foam are already known in several areas, such as pesticide reservoirs, fire extinguishers, shaving foam, and others. These containers have different sizes and characteristics that suit each functionality, with different means of recharge or creation of foam.

Today, professionals in the field are aware of the use of "three-way taps" in endovascular treatments to create homemade sclerosing foam adaptable directly to syringes, where the connection is done and the direction of the flow is controlled with three different lines: two infusion lines in "luer lock" female ends, and a third infusion line or venous access device in its male "luer slip" or "luer lock" connection. It also includes a knob that acts as flow shutter and switch.

Patent application BR 0407003-8, filed on Aug. 19, 2004, describes a foam forming unit comprised of: a mixing chamber (12) that communicates with the output (14) of a pump in order to mix liquid and air, a distribution part (22) equipped with an output flow channel (24) with a foam opening (26) to distribute foam, where the output flow channel has communication with the mixing chamber (12) and the first foam forming element (28) placed in the output flow channel, so that the foam that flows through the output flow channel passes through the foam forming element (28) at least twice, where the distribution part is also equipped with a nozzle element (51) that includes at least a final part of the output flow channel and the foam opening, where the output flow channel includes a cavity (32) after the first passage through the first foam forming element, with this cavity positioned before the nozzle element, as observed in the flow direction.

Patent application BR 0414281-0, filed on Sep. 9, 2004, describes a foam transfer device (600) to be used with an aerosol containing device to produce sclerosing foam for the treatment of varicose veins, among other things. This device enables the deviation of an initial quantity of foam with the specification below from the container to be dispensed, for instance, into a full dispensing changer before releasing an additional quantity of foam to be used in treatments. The flow switching from the dispensing chamber to a different output (618) for use is done without interruption in the flow from the aerosol container, as this causes the foam to go down under specification again. The dispensing chamber may be transparent, so that the foam entering it can be observed, allowing the user to decide when to stop sending foam to be dispensed. Alternatively, the foam can be deviated automatically, for instance, at the end of a preset time or present volume of foam to be dispensed. The foam is usually released into a syringe for injection into a varicose vein of the patient.

In view of the techniques and devices found in the current state of art, the applicant proposes an unprecedented mixing device used to create sclerosing foam with microbubbles, also introducing advantages and improvements to the deficiencies found in the current techniques and models.

BRIEF DESCRIPTION OF THE FIGURES

For better visualization and understanding of the object intended to be protect by this patent application, the object will be described below with the aid of the attached figures

DETAILED DESCRIPTION AND ADVANTAGES OF THE DEVICE

This patent application is explained in details in accordance with the attached figures.

Figure 1:
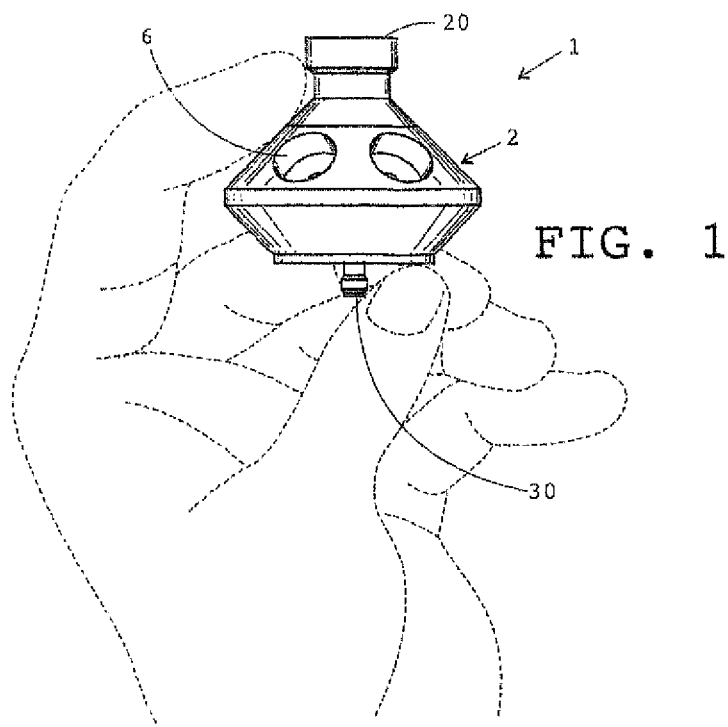
FIG. 1 illustrates a side view of the mixing device in a first embodiment, as held by the hand of a professional.
Figure 2:
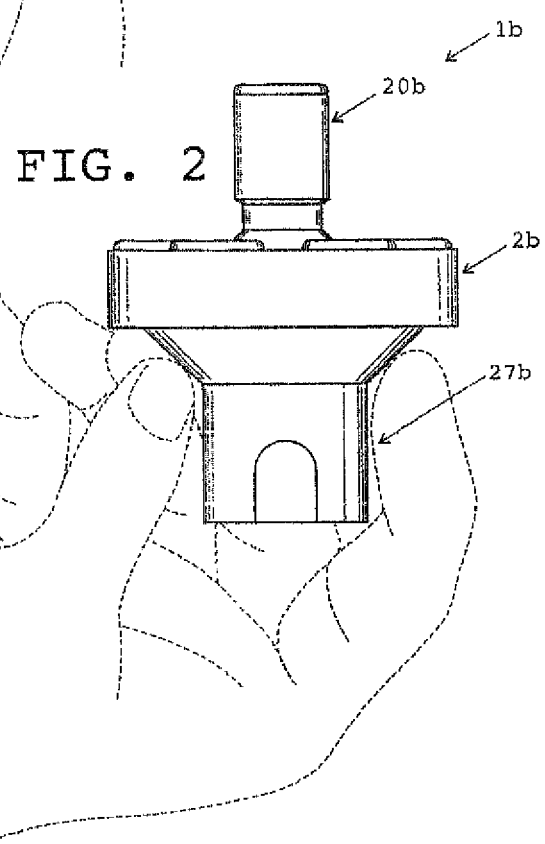
FIG. 2 illustrates a side view of the mixing device in a second embodiment, as held by the hand of a professional.

FIG. 1 shows an embodiment of the object of this patent application with a front view of the rechargeable, resterilizable mixing device, with physiological solution and gas to create foam with microbubbles used in endovascular treatments. FIG. 2 shows a different embodiment from the object shown in FIG. 1.

According to FIGS. 3 to 6, the mixing device (1) claimed in this patent application comprises a body (2) with the shape of two inverted cones joined by their bases, a central cylindrical channel (3) and inclined downward channels (4) that intercept the central cylindrical channel (3) at its bottom end (5). The inclined downward channels (4) include a cylindrical recess (6) in its top end to receive the syringe body by coupling.

The mixing device (1) also includes a central valve support (7), a cylindrical base (9), and a head (8) in the shape of a cone. The base (9) of the central support (7) has a sealing ring (10) on the outer surface and an internal opening (11) inside it, which crosses the central valve support (7) throughout its length. This opening (11) has a cylindrical recess (12) in its bottom end with an upward conical protrusion (13) that reaches half the length of the central support (7). Between the conical protrusion (13) and the cylindrical recess (12) there is a conical recess (14) that includes an inclined through hole (15), which enables the communication between the internal opening (11) with the external cylindrical surface of the central support (7). Above the conical protrusion (13) there is a cylindrical channel (16) that communicates with the head seat opening (17), located in the region of the head (8) of the central support (7). This head seat opening (17) includes conical housing recesses (18) in which the conical tip of the head (21) seats to form small passing openings (22) for the foam with microbubbles.

Figure 4:
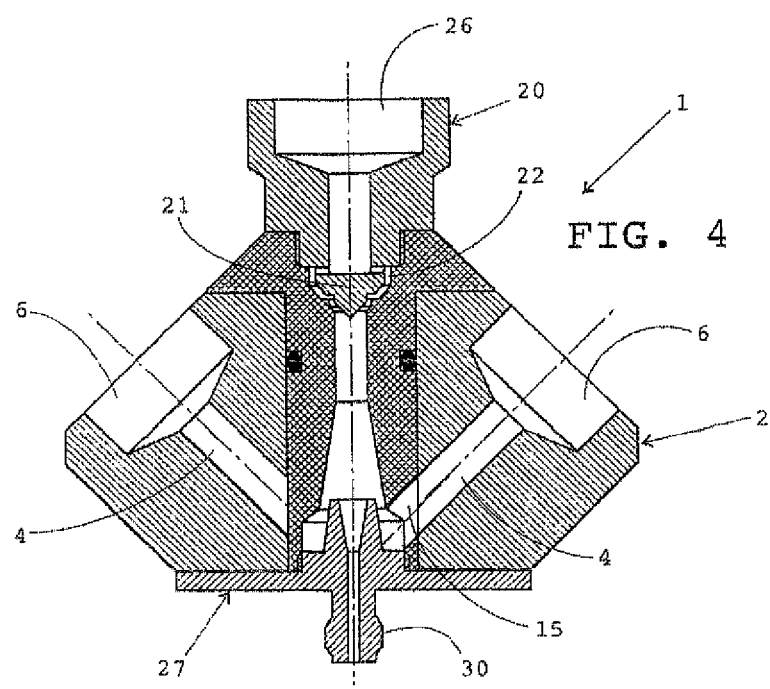
FIG. 4 shows the cross sectional view A-A indicated in the previous figure.
Figure 5:
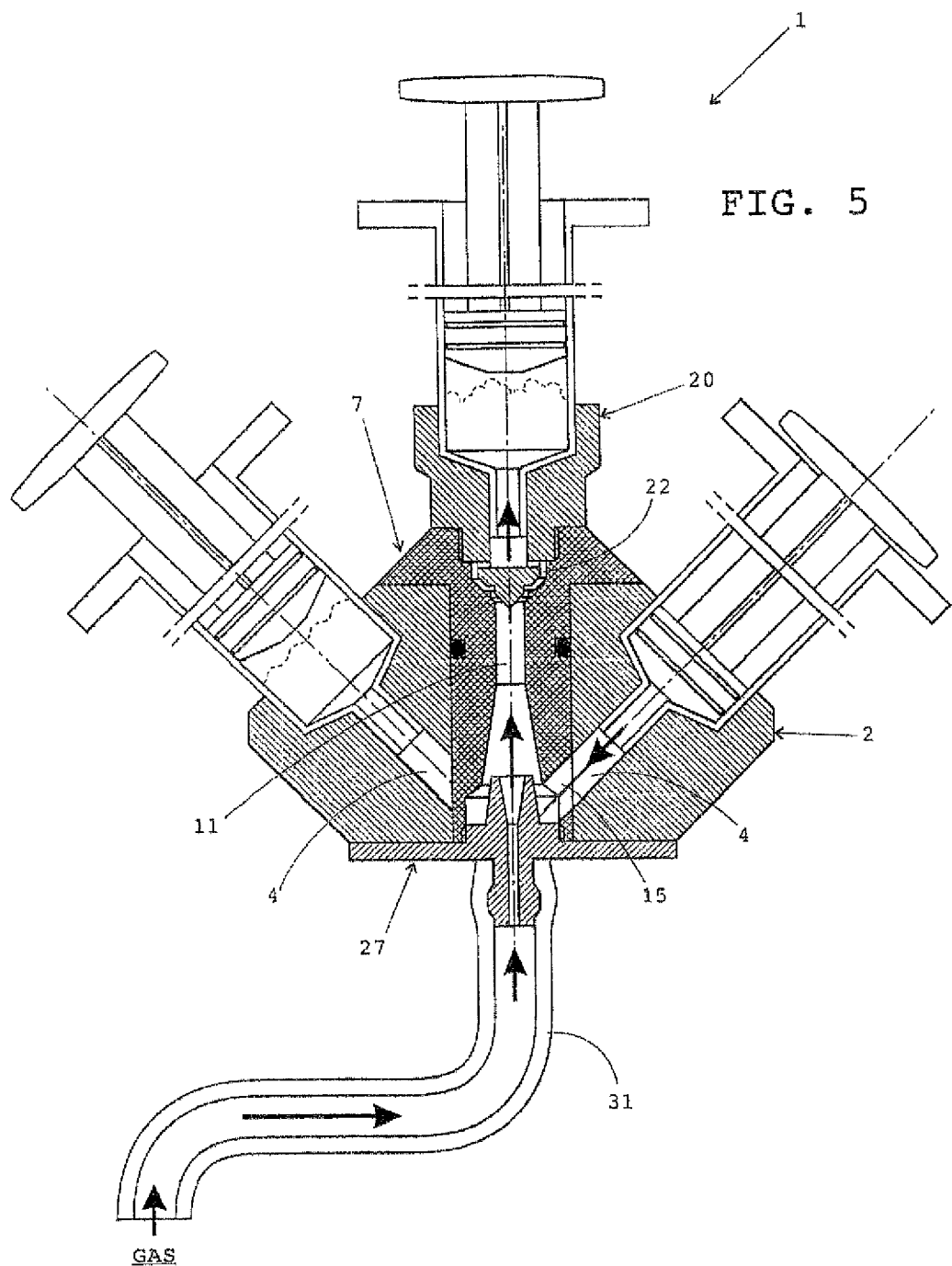
FIG. 5 shows a cross sectional view of the device in the previous figure being used.
Figure 6:
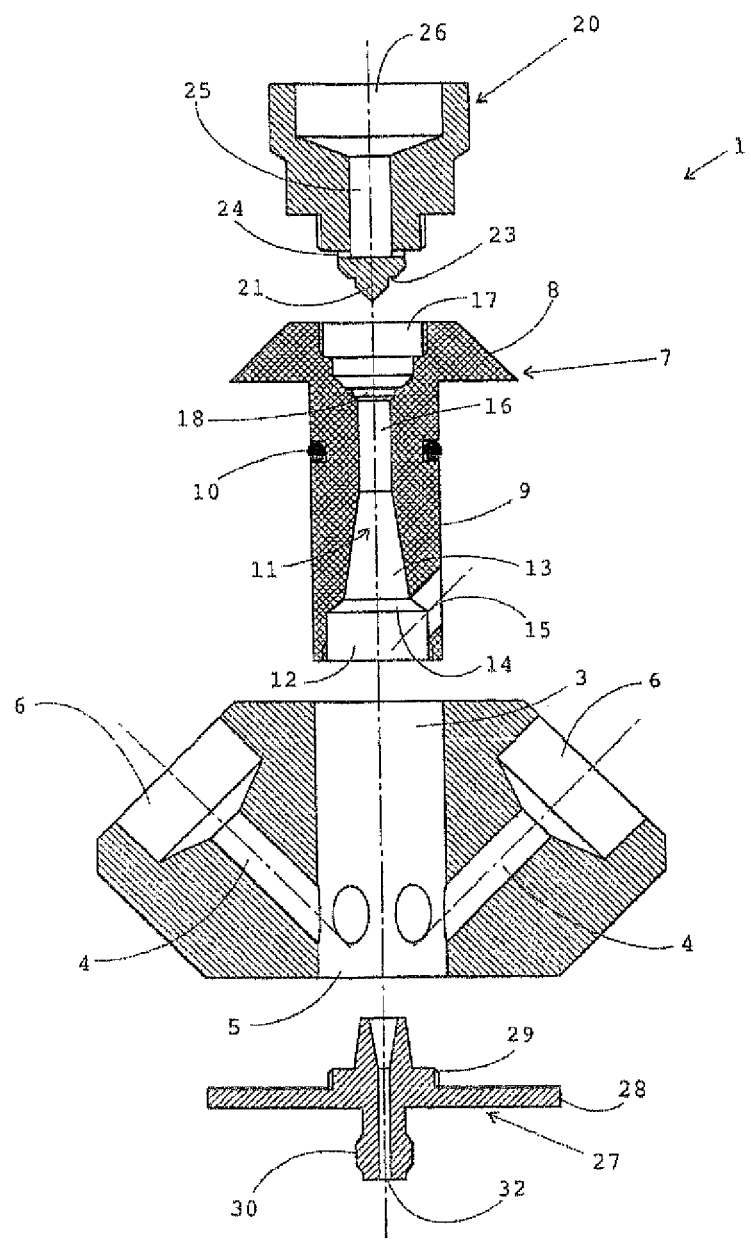
FIG. 6 shows an exploded view of the device in its first embodiment, according to the previous figure.

The head (20) is comprised of a cylindrical part with a tip (21) of staggered conical shape that forms a step (23) in its middle region to enable the formation of the passing channel (22) of the foam with microbubbles (FIGS. 4 and 5). Above the tip (21) there are openings (24) that communicate with the luer channel (25) that receives the external part of the syringe to be fitted into the orifice (26) of the head (20).

At the bottom of the device (1) a connector (27) is connected and comprised of a thin cylindrical disc (28) that is supported by the bottom part of the body (2) and couples into the internal opening (11) of the central valve support (7) by means of a threaded protrusion (29). This connector (27) has a fitting nozzle (30) in its bottom part to receive a hose (31), through which a gas enters and flows into the internal opening (11) of the central valve support (7) through the passage (32).

Figure 3:
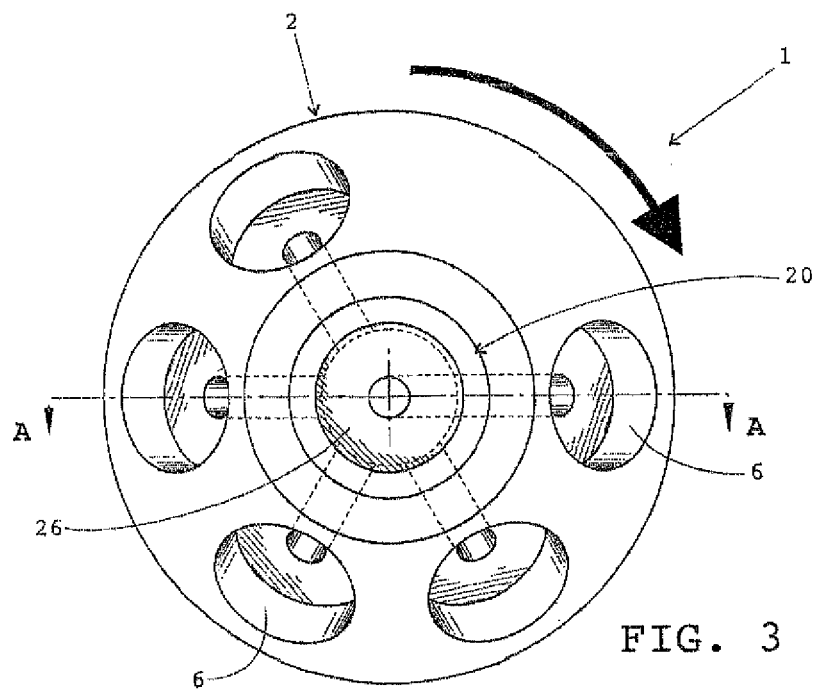
FIG. 3 shows a top view of the device in its first embodiment, indicating the cross section A-A.

FIGS. 3, 4, and 5 explain the operation of the mixing device (1). The arrow in FIG. 1 indicates the direction of rotation of the body (2) to which the syringes shown in FIG. 5 are coupled. These syringes contain several solutions with different concentration levels to form the foam with microbubbles. It is possible to observe that each inclined downward channel. (4) in the body (2) communicates with the internal opening (11) through the inclined passing hole (15) of the central valve support. Each rotation of the body (2) presents a single inclined downward channel (4) that communicates with the through hole (15). Therefore, only a given syringe containing a solution with a given concentration level will have fluid communication with the opening (11) and consequently with the passage of gas (32) and luer channel (25). The gas flow causes the solution to flow through the narrow passages (22), enabling the formation of the microbubbles in the foam that enter the syringe inserted into the head (8). Alternatively, to assist in the formation of microbubbles, a small sponge of micro-porous material can be placed in the luer channel (25).

Figure 7:
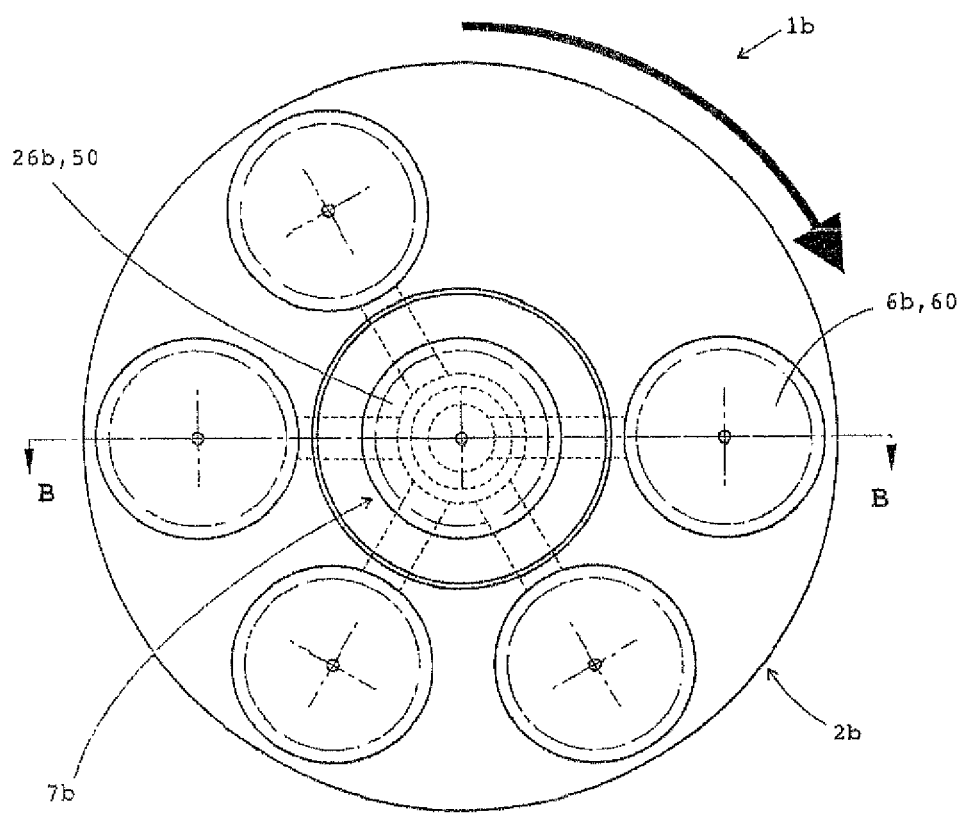
FIG. 7 shows a top view of the device in its second embodiment, indicating the cross section B-B.
Figure 8:
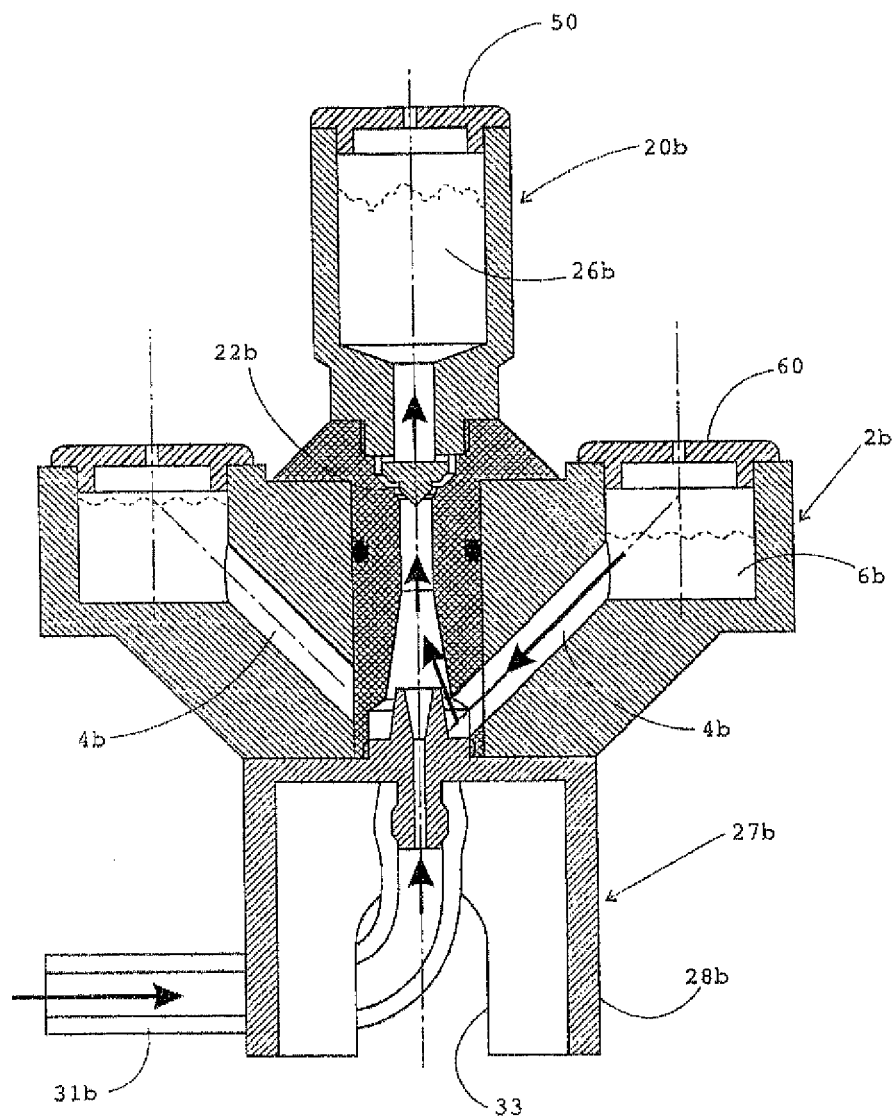
FIG. 8 shows the cross section B-B indicated in the previous figure with the device being used.
Figure 9:
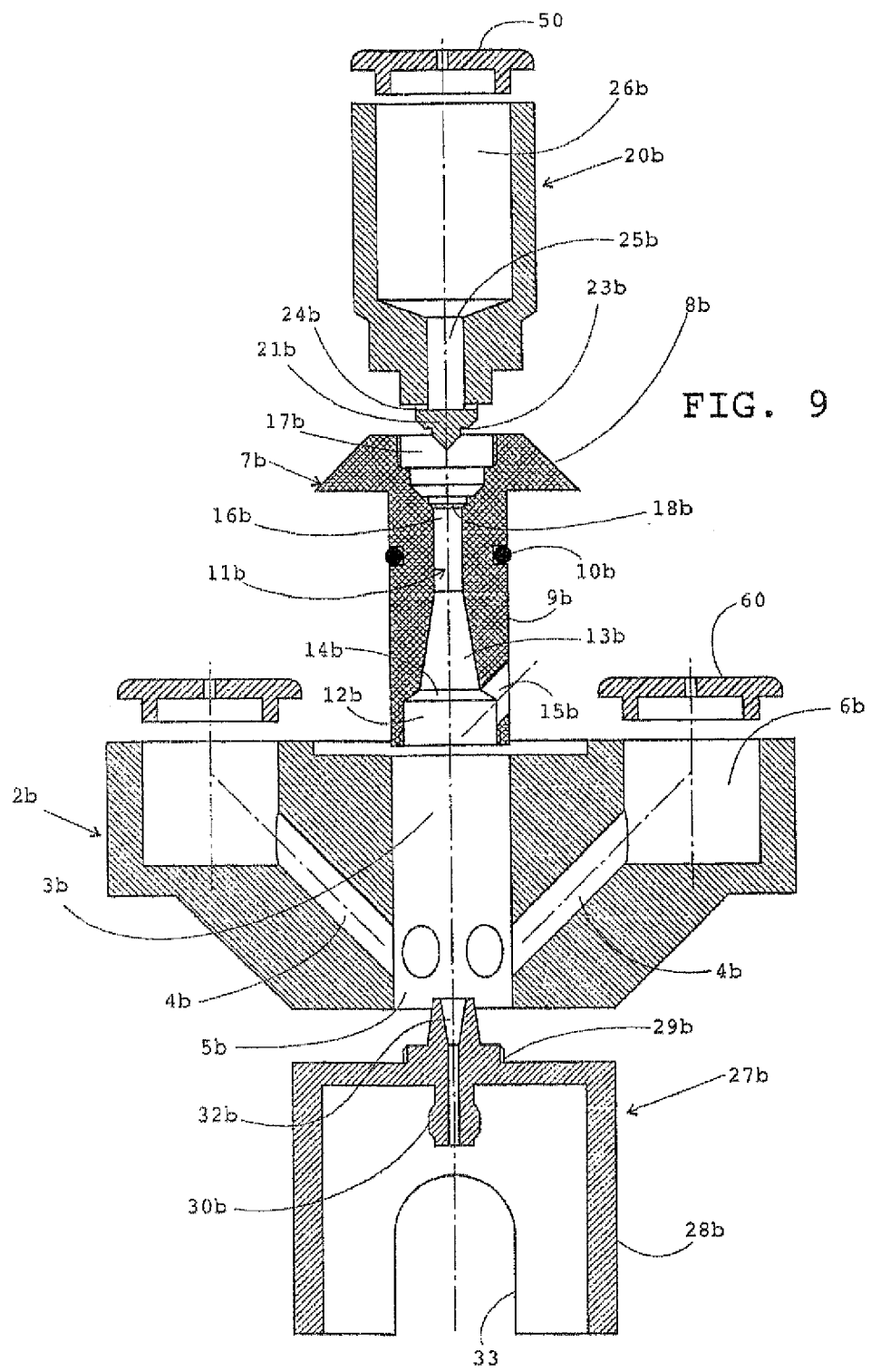
FIG. 9 shows an exploded view of the device in its second embodiment, according to the previous figure.

FIGS. 7, 8, and 9 show an embodiment of the object of the rechargeable, resterilizable mixing device with physiological solution and gas to create foam with microbubbles used in endovascular treatments. In this embodiment, the mixing device (1b) comprehends a body (2b) with cylindrical shape on the top part and the shape of an inverted cone body on the bottom part, with a central cylindrical channel (3b) and inclined downward channels (4b) that intercept the central cylindrical channel (3b) at its bottom end (5b). These inclined channels (4b) include a cylindrical recess (6b) at their top ends in order to receive a hermetic lid (60) by coupling fit.

The mixing device (1b) also includes a central valve support (7b), a cylindrical base (9b), and a head (8b) in the shape of a cone. The base (9b) of the central support (7b) has a sealing ring (10b) on the outer surface and an internal opening (11b) inside it, which crosses the central valve support (7b) throughout its length. This opening (11b) has a cylindrical recess (12b) in its bottom end with an upward conical protrusion (13b) that reaches half the length of the central support (7b). Between. this conical protrusion (13b) and the cylindrical recess (12b) there is a conical recess (14b) that includes an inclined through hole (15b), which enables the communication between the internal opening (11b) and the external cylindrical surface of the central support (7b). Above the conical protrusion (13b) there is a cylindrical channel (16b) that communicates with the head seat opening (17b), located in the region of the head (8b) of the central support (7b). This head seat opening (17b) includes conical housing recesses (18b) in which the conical tip of the head (21b) seats to form small passing openings (22b) (FIG. 8) for the foam with microbubbles.

The head (20b) is comprised of a cylindrical part with a tip (21b) of staggered conical shape that forms a step (23b) in its middle region to enable the formation of the passing channel (22b) of the foam with microbubbles (FIG. 8). Above the tip (21b) there are openings (24b) that communicate with the leer channel (25b) that receives the external part of the syringe to be fitted into the orifice (26b) of the head (20b). This opening also receives a hermetic lid (50).

At the bottom of the device (1b) a connecting base (27b) is connected and comprised of a cylindrical lid (28b) that is supported by the bottom part of the body (2b) and couples into the internal opening (11b) of the central valve support (7b) by means of a threaded protrusion (29b). Internally, this lid (28b)

contains a fitting nozzle (30b) to receive a hose (31b), through which a gas enters and flows through the passage (32b) into the internal opening (11b) of the central valve support (7b). The cylindrical lid (28b) has a groove (33) on its side to receive the gas hose (31b).

The operation of the next device (1b) is similar to the description of the device above (1), differing only by the fact that, in lieu of syringes, the solutions are placed in small reservoirs (6b) contained in the body (2b). The foam formed with microbubbles is stored in the head (20b).

Therefore, as observed in the description detailed above, the device is comprised of a set of disassemblable and interchangeable parts that lock against each other for easy sterilization and handling, and resistance against extremely low or high temperatures. The device at hand is fully mounted on the body (2,2b) around an essentially cylindrical axle comprised of the central valve support (7,7b), while the top conical body portion comprehending the head (8,8b) is crossed in its center by a flow orienting duct (25, 25b). This axle, comprised of the central valve support (7,7b), is coupled at the center of a spinning circular reservoir constituted of the body (2,2b), containing several housings (6,26) for the application of several solutions with different concentration levels. These parts are locked by a connector (27) at the bottom to the gas duct (31) with a spray nozzle. Each housing (26) has a channel (4) that can be aligned to communicate with the inside of the flow orienting duct (11) of the central axle (7), responsible for orienting the produced mixture to a top reservoir with a foam-making nozzle.

The invention claimed is:

1. Rechargeable, resterilizable mixing device for mixing a physiological solution and a gas to create foam with microbubbles for use in endovascular treatments, the mixing device comprising a body in the shape of two inverted cones united by their bases, with a central cylindrical channel and inclined downward channels that intercept the central cylindrical channel at a bottom end of the body, the inclined downward channels containing a cylindrical recess at a top end, the mixing device further including a central valve support having a cylindrical base and a cone-shaped head, the cylindrical base of the central valve support including a sealing ring on an external surface and including an internal opening crossing a length of the central valve support, the internal opening having a cylindrical recess on a bottom end of the central valve support with a conical protrusion extending upward until a middle region of the length of the central valve support, the internal opening including a conical recess disposed between the conical protrusion and the cylindrical recess, the conical recess containing an inclined passage hole that enables communication between the internal opening and the external cylindrical surface of the central valve support, a cylindrical channel is disposed above the conical protrusion and communicates with an opening of a head seat (17), located in a region of the cone-shaped head of the central valve support, the opening of the head seat contains conical housing recesses to receive a conical tip of a head piece, thereby forming small passage openings the head piece including a cylindrical part with a staggered conical tip that forms a step adjacent a middle and enabling the formation of the small passage openings, openings are included above the tip that communicate with a luer channel, adjacent a bottom part of the mixing device there is a coupled connector comprising a thin cylindrical disk supported by the bottom end of the body and coupled with the internal opening of the central valve support by means of a threaded protrusion the coupled connector including a fitting nozzle to receive a hose.

2. Rechargeable, resterilizable mixing device for mixing a physiological solution and gas to create foam with microbubbles for use in endovascular treatments, the mixing device comprising a body (2b) with cylindrical shape on a top part and the shape of an inverted cone body on a bottom part, the mixing device including a central cylindrical channel and inclined downward channels that intercept the central cylindrical channel at a bottom end of the central cylindrical channel, the inclined downward channels include a cylindrical recess at their top ends in order to receive a hermetic lid, the mixing device also including a central valve support having, a cylindrical base and a head in the shape of a cone, the cylindrical base of the central valve support including a sealing ring on an external surface of the central valve support and an internal opening which crosses a length of the central valve support, the opening including a cylindrical recess in a bottom end of the central valve support with an upward conical protrusion that reaches half the length of the central valve support, a conical recess is disposed between the conical protrusion and the cylindrical recess, the conical recess containing an inclined passage hole, above the conical protrusion there is a cylindrical channel that communicates with a head seat opening located in a region of the head of the central valve support, the head seat opening including conical housing recesses in which a conical tip of a head piece seats to form small passing openings the head piece being comprised of a cylindrical part with the conical tip having a staggered conical shape that forms a step in its middle region, above the tip there are openings that communicate with a luer channel, adjacent a bottom of the device a connecting base is connected, the connecting base including a cylindrical lid that is supported by the bottom part of the body and couples into the internal opening of the central valve support by means of a threaded protrusion (29b), the lid including a fitting nozzle and a side groove.

* * * * *

UNITED STATES PATENT AND TRADEMARK OFFICE
CERTIFICATE OF CORRECTION

PATENT NO. : 8,882,086 B2  
APPLICATION NO. : 13/580202  
DATED : November 11, 2014  
INVENTOR(S) : Caporal Piotrovski Page 1 of 1

It is certified that error appears in the above-identified patent and that said Letters Patent is hereby corrected as shown below:

In the Claims:

At Column 6, line 5, Claim 1, "piece," should be -- piece --.

At Column 6, line 17, Claim 2, "gas to" should be -- a gas to --.

At Column 6, line 26, Claim 2, "having," should be -- having --.

Signed and Sealed this
Ninth Day of February, 2016

Michelle K. Lee
*Director of the United States Patent and Trademark Office*